United States Patent
Agathos

(10) Patent No.: US 11,103,619 B2
(45) Date of Patent: Aug. 31, 2021

(54) ANTICALCIFICATION TREATMENT FOR IMPANTABLE BIOLOGICAL TISSUES USING CALCITONIN

(71) Applicant: Efstathios-Andreas Agathos, Athens (GR)

(72) Inventor: Efstathios-Andreas Agathos, Athens (GR)

(73) Assignee: Efstathios-Andreas Agathos, Athens (GR)

( * ) Notice: Subject to any disclaimer, the term of this patent is extended or adjusted under 35 U.S.C. 154(b) by 398 days.

(21) Appl. No.: 16/117,413

(22) Filed: Aug. 30, 2018

(65) Prior Publication Data

US 2020/0069842 A1 Mar. 5, 2020

(51) Int. Cl.
*A61L 27/36* (2006.01)
*A61L 27/50* (2006.01)
*A61F 2/24* (2006.01)

(52) U.S. Cl.
CPC ......... *A61L 27/3687* (2013.01); *A61L 27/367* (2013.01); *A61L 27/3612* (2013.01); *A61L 27/3625* (2013.01); *A61L 27/3641* (2013.01); *A61L 27/3654* (2013.01); *A61L 27/507* (2013.01); *A61F 2/2412* (2013.01); *A61L 2400/02* (2013.01); *A61L 2430/06* (2013.01); *A61L 2430/20* (2013.01)

(58) Field of Classification Search
CPC .. A61L 27/36; A61F 27/3687; A61F 27/3612; A61F 27/3625
See application file for complete search history.

(56) References Cited

U.S. PATENT DOCUMENTS

| | | | |
|---|---|---|---|
| 4,120,649 A | 10/1978 | Schechter | 8/94.11 |
| 4,648,881 A | 3/1987 | Carpentier et al. | 128/898 |
| 4,885,005 A | 12/1989 | Nashef et al. | 8/94.11 |
| 4,976,733 A | 12/1990 | Girardot | 623/11.11 |
| 5,002,256 A | 3/1991 | Bedford | 254/2 R |
| 5,330,909 A * | 7/1994 | Yamashita | C07K 16/26 435/336 |
| 6,165,216 A | 12/2000 | Agathos | 623/2.13 |
| 2008/0319166 A1 | 12/2008 | Shen | 530/345 |
| 2019/0374650 A1* | 12/2019 | Moon | A61K 39/39 |
| 2021/0128473 A1* | 5/2021 | Thuresson | A61K 9/0014 |

FOREIGN PATENT DOCUMENTS

| | | |
|---|---|---|
| EP | 103947 A2 | 3/1984 |
| GR | 1006462 | 6/2009 |
| WO | WO 84/01879 | 5/1984 |
| WO | WO/1996/004028 | 7/1984 |

OTHER PUBLICATIONS

Agathos and Starr "Mitral Valve Replacement." *Curr Probl Surg*, 30(6):481-592 (1993).
Agathos, et al., "In Vivo Calcification of Glutaraldehyde-Fixed Cardiac Valve and Pericardium of Phoca Groenlandica." *Asaio J*, 57(4):328-332 (2011).
Guide for the Care and Use of Laboratory Animals prepared by the Institutes of Laboratory Animal Resources, National Research Council and published by the National Academy Press, NIH publication No. 85-23 revised 1996, pp. i-xii and 1-57 (1996a).
Guide for the Care and Use of Laboratory Animals prepared by the Institutes of Laboratory Animal Resources, National Research Council and published by the National Academy Press, NIH publication No. 85-23 revised 1996, pp. i (repeat), 58-128, (1996b).
Jamieson "Modern Cardiac Valve Devices-Bioprostheses and Mechanical Prostheses: State of the Art." *J Card Surg*, 8(1):89-98 (1993).
Levy, et al., "Biologic Determinants of Dystrophic Calcification and Osteocalcin Deposition in Glutaraldehyde-Preserved Porcine Aortic Valve Leaflets Implanted Subcutaneously in Rats." *Am J Pathol*, 113(2):143-155 (1983).
Manji, et al., "Glutaraldehyde-Fixed Bioprosthetic Heart Valve Conduits Calcify and Fail from Xenograft Rejection." *Circulation*, 114(4):318-327 (2006).
Mueller and von Segesser "A New Equine Pericardial Stentless Valve." *J Thorac Cardiovasc Surg*, 125(6):1405-1411 (2003).
Pearse "The Cytochemistry of the Thyroid C Cells and Their Relationship to Calcitonin." *Proc R Soc Lond B Biol Sci*, 164(996):478-487 (1966).
Potts "Chemistry of the Calcitonins." *Bone Miner*, 16(3):169-173 (1992).
Schoen and Levy "Calcification of Tissue Heart Valve Substitutes: Progress toward Understanding and Prevention." *Ann Thorac Surg*, 79(3):1072-1080 (2005).
Agathos,[1] "The role of Calcitonin and Parathormone during the transient hypocalcemia following total thyroidectomy". PhD Thesis, University of Athens Medical School, 1988, Doi 10.12681/eadd/9351.
Jamieson "Modem Cardiac Valve Devices—Bioprostheses and Mechanical Prostheses: State of the Art." *J Card Surg*, 8(1):89-98 (1993).
Tissue Heart Valves,[2] ed. By M. I. Ionescu, publisher Butterworth Inc., Boston, Mass., U.S.A., particularly at pp. 146-172 (1979).
Weinhold,[3]et al., "Kangaroo Xenobioprostheses—an Advantage in Heart Valve Replacement." *Z Kariol*, 75 Suppl 2:251-253 (1986).

* cited by examiner

*Primary Examiner* — Jason-Dennis N Stewart

(74) *Attorney, Agent, or Firm* — Medlen & Carroll, LLP

(57) ABSTRACT

This invention relates to the field of surgical implants, and in particular to a method of treating biomedical material, and more particularly bioprosthetic heart valves and tracheas, to mitigate calcification when implanted in a mammalian body.

23 Claims, No Drawings

ANTICALCIFICATION TREATMENT FOR IMPANTABLE BIOLOGICAL TISSUES USING CALCITONIN

FIELD OF INVENTION

This invention relates to the field of surgical implants, and in particular to a method of treating biomedical material, and more particularly bioprosthetic heart valves and tracheas, to mitigate calcification when implanted in a mammalian body.

BACKGROUND

Calcification remains the major role of failure of implantable biomedical material and in particular of bioprosthetic valves. Bioprosthetic heart valves may be constructed either from porcine aortic valves, or bovine pericardium (W. R. E. Jameison: *J. Cardiac Surgery.*, 1993; 8; 89-98). New animals have been tested such as Kangaroo (C. Weinhold et al., *Z. Kardiol.* 75, *Suppl.* 2, pp 251-253, 1986), seal aortic and pulmonary valves as well as pericardium (U.S. Pat. No. 6,165,216, Agathos E. A.: *Human Cardiac Valve Placement with Marine Mammal Ventricular Outflow (Aortic or Pulmonary) Valve*) and Equine pericardium (Xavier M. Mueller, Ludwig K. von Segesser: *A new equine pericardial stentless valve* J Thorac Cardiovasc Surg 2003; 125:1405-1411). Other implantable biological tissue can either be bovine, equine or seal pericardium to close cardiac defects, arterial conduits of various animal sources for arterial bypass purposes, seal tracheas to replace large tracheal defects (Greek Patent No. 1006462 Agathos E. A.: *A Novel Bioprosthetic Trachea Derived From Seal Trachea*), and skin grafts from human cadavers.

Bioprosthetic heart valves have been widely used to replace diseased cardiac valves over the past 30 years because of their excellent hemodynamics, safety of insertion, low risk of infective endocarditis, and low rate of thromboembolism without long-term anticoagulation (Schoen F J, Levy R J: *Calcification of tissue heart valves substitutes: Progress toward understanding and prevention.* Annals Thoracic Surgery 79: 1072-1080, 2005).

These advantages, however, are frequently undermined by the relative high rate of valve failure because of progressive calcification and degeneration of the valve cusps, particularly in younger patients (<65 years) and the pediatric population (Agathos E A, Starr A: *Mitral valve replacement. Current Problems in Surgery* 30: 481-592, 1993). One of the mechanistic factors responsible for bioprosthetic cuspal calcification is glutaraldehyde fixation. (Levy R J, Schoen F J, Levy J T, et al: *Biolofical determinants of dystrophic calcification and osteocalcin deposition in glutaraldehyde-preserved porcine aortic valve leaflets implanted subcutaneously in rats. American Journal of Pathology* 113:143-155, 1983). A strong relationship exists between inflammatory infiltration (e.g. macrophages) and calcification in glutaraldehyde-fixed bioprosthetic valves (Manji R A, Zhu L F, Nijjar N K, et al: *Glutaradehyde-fixed bioprosthetic heart valves conduits calcify and fail from xenograft rejection.* Circulation 114:318-327, 2006).

Various treatments have been proposed to mitigate calcification of glutaraldehyde-fixed bioprosthetic valves and some methods are described in U.S. Pat. No. 4,885,005 (Nashef et al: Surfactant Treatment of Implantable Biological Tissue to inhibit Calcification), U.S. Pat. No. 4,648,881 (Carpentier et al: Implantable Biological Tissue and process for Preparation Thereof), U.S. Pat. No. 4,976,733 (Girardot: Prevention of Prosthesis Calcification), U.S. Pat. No. 4,120,649 (Schechter: Transplants), U.S. Pat. No. 5,002,256 (Carpentier: Calcification Mitigation of Bioprosthetic Implants), EP 103947A2 (Pollock et al: Method of Inhibiting Mineralization of Natural Tissue During Implantation), WO 84/01879 (Nashef et al: Surfactant Treatment of Implantable Biological Tissue to Inhibit Calcification), WO 9604028A1 (Carpentier et al: Methods For Treating Implantable Biological Tissues To Mitigate The Calcification Thereof), Patent Application 20080319166 (Shen: Treatment of Implantable Medical Devices Resistant To Calcification).

None of the above proposed though treatments have succeeded. What is needed is a way for inhibiting or mitigating efficiently the calcification process of the implantable biological tissues.

SUMMARY OF THE INVENTION

This invention relates to the field of surgical implants, and in particular to a method of treating biomedical material, and more particularly bioprosthetic heart valves and tracheas, to mitigate calcification when implanted in a mammalian body.

The present invention alleviates the deficiencies associated with prior art. More particularly, the present invention, in one embodiment, comprises a method associated with treating glutaraldehyde-fixed biological tissue, or biological tissue fixed with other chemicals, thus eliminating or mitigating the calcification process following implantation into the mammalian body. In one embodiment, the method comprises placing the biological tissue for fixation and preservation in a buffered glutaraldehyde (Glut) solution (e.g. 0.5% at pH 7.4) and adding calcitonin. It is not intended that the present invention be limited to any particular source of calcitonin. However, salmon synthetic calcitonin (CT) is a convenient source. While some have suggested the use of additional compounds, such as an eNOS activator and/or an anti-proliferative agent, such compounds are not needed and are preferably lacking in the treatment contemplated herein.

In another embodiment, the method comprises of placing the biological tissue, after fixed with glutaraldehyde or other fixative compounds, in contact with Calcitonin solution for a time between 4 hours up to 36 hours at a temperature between 17° up to 34° C.

It is not intended that the present invention be limited to any particular mechanism by which the treatment method works. Nonetheless, it is believed that the treatment allows for the synthesis of adducts with aldehyde groups, thus (perhaps permanently) eliminating the places of the biological tissue onto the calcium cations could deposit.

Thus, in one embodiment, the present invention contemplates a method for treating biological tissue, comprising exposing said tissue to a mixture of a fixative and Calcitonin in solution so as to create treated biological tissue. It is not intended that the present invention be limited to the nature of the biological tissue. However, preferred biological tissues are those used for heart valve implants. It is not intended that the present invention be limited to the nature of the fixative. However, a preferred fixative is glutaraldehyde. It is not intended that the present invention be limited as to the nature of source of said Calcitonin. In one embodiment, said Calcitonin is human Calcitonin. In another embodiment, said Calcitonin is synthetic Calcitonin. In one embodiment, said Calcitonin is salmon Calcitonin. It is not intended that the present invention be limited to the amount of time the tissue is exposed to the solution. However, in one embodiment, said exposing is for a time period between 4 and 36 hours. It is also not intended that the present invention be limited to the particular conditions used during the exposing. However, in one embodiment, said exposing is done at a temperature between 17° and 37° C. In one embodiment, the solution is stirred during said exposing (e.g. stirring is between 50 rpm and 100 rpm). In a preferred embodiment, the method further comprises implanting said treated biological tissue in a human or animal so as to create an implanted biological tissue. Of course, the tissue can be subjected to additional treatments (e.g. rinsing, sterilization, etc.) prior to said implanting, if desired. A variety of tissue types and tissue sources are contemplated. In one embodiment, said implanted biological tissue is selected from the group consisting of porcine aortic valves and pericardium, bovine pericardium, equine pericardium, seal aortic, pulmonary valve and pericardium, kangaroo aortic valve and pericardium and seal trachea. In one embodiment, conduits are contemplated for treatment and implantation. In one embodiment, said implanted biological material comprises one or more arterial conduits of human or animal origin.

In a preferred embodiment, the present invention contemplates a method for treating biological tissue, comprising a) exposing said tissue to a mixture of a fixative and Calcitonin in solution so as to create treated biological tissue; and b) implanting said treated biological tissue in a human or animal so as to create implanted biological tissue. It is not intended that the present invention be limited to the nature of the biological tissue. However, preferred biological tissues are those used for heart valve implants. It is not intended that the present invention be limited to the nature of the fixative. However, a preferred fixative is glutaraldehyde. It is not intended that the present invention be limited as to the nature of source of said Calcitonin. In one embodiment, said Calcitonin is human Calcitonin. In another embodiment, said Calcitonin is synthetic Calcitonin. In one embodiment, said Calcitonin is salmon Calcitonin. It is not intended that the present invention be limited to the amount of time the tissue is exposed to the solution. However, in one embodiment, said exposing is for a time period between 4 and 36 hours. It is also not intended that the present invention be limited to the particular conditions used during the exposing. However, in one embodiment, said exposing is done at a temperature between 17° and 37° C. In one embodiment, the solution is stirred during said exposing (e.g. stirring is between 50 rpm and 100 rpm). It is not intended that the method be limited to just two steps. For example, in one embodiment, the method further comprises rinsing said treated biological tissue after step a) and before step b). Once again, a variety of tissue types and tissue sources is contemplated. In one embodiment, said implanted biological tissue is selected from the group consisting of porcine aortic valves and pericardium, bovine pericardium, equine pericardium, seal aortic, pulmonary valve and pericardium, kangaroo aortic valve and pericardium and seal, porcine and dog trachea. In one embodiment, conduits are treated and implanted. In one embodiment, said implanted biological material comprises one or more arterial conduits of human or animal origin. In one embodiment, said implanted biological material comprises one or more venous conduits of human or animal origin.

In yet another embodiment, the present invention contemplates a method for treating glutaraldehyde fixed implantable biological tissues to inhibit calcification of the tissue following implantation in a mammalian body, the method comprising the steps of forming adducts with aldehyde groups and Calcitonin, thus permanently eliminating the places of the biological tissue onto the Calcium cations could deposit. In one embodiment, the adducts with aldehyde groups are formed when Calcitonin is added in the fixed implantable biological tissues. In one embodiment, Calcitonin is used during or after the fixation process. In one embodiment, Calcitonin is used with glutaraldehyde or other fixation compound. In one embodiment, the Calcitonin is human Calcitonin. In one embodiment, the Calcitonin is synthetic. In one embodiment, Calcitonin comes from salmon or some other animal. In one embodiment, the time period for the anticalcification treatment can be between 4 and 36 hours. In one embodiment, the temperature of the process is between 17° and 37° C. In one embodiment, the reaction process takes place in a quiet environment. In one embodiment, the reaction process takes place with stirring the solution between 50 rpm and 100 rpm. In one embodiment, the implantable biological tissues is selected from the group consisting of porcine aortic valves and pericardium, bovine pericardium, equine pericardium, seal aortic, pulmonary valve and pericardium, kangaroo aortic valve and pericardium and human, seal, porcine and dog trachea. In one embodiment, arterial conduits of various animal sources or of human origin are used as implantable biological material.

DEFINITIONS

As used herein, the term "valve" is a structure that regulates, directs or controls the flow of a fluid. A "heart valve" may refer to any of the four main heart valves that prevent the backflow of blood during the rhythmic contractions. The four main heart valves are the tricuspid, pulmonary, mitral, and aortic valves. The tricuspid valve separates the right atrium and right ventricle, the pulmonary valve separates the right atrium and pulmonary artery, the mitral valve separates the left atrium and left ventricle, and the aortic valve separates the left ventricle and aorta. Thus, in one aspect, the bioprosthetic valve and the diseased valve may be an aortic valve, pulmonary valve, tricuspid valve, or mitral valve. The aortic valve normally has three cusps or leaflets. Materials used for bioprosthetic heart valves include, but are not limited to, bovine pericardial and/or porcine aortic valve cusps.

The first decision that surgeons are often called to make is whether to use a venous or an arterial "conduit." In general, the main advantage of arterial grafts is their superior long-term patency compared with saphenous vein grafts (SVGs) and, accordingly, arterial grafts are more indicated in younger patients or in those who have a life expectancy of more than 10 years, which is beyond the benefit of SVGs. On the other hand, the technique of arterial grafting is more challenging and time-consuming, and therefore venous grafting is preferred in emergency situations and for patients with a higher operative risk.

While vein grafts act merely as conduits, arterial grafts have the ability to adapt to different demands of blood supply and show specific functional properties. The structure of the arteries differs in elastic and muscular composition, thus some are more reactive to vasoconstrictors than others.

The present invention contemplates the treatment of valves and conduits (both venous and arterial) with Calcitonin (as described in more detail below).

GENERAL DESCRIPTION

This invention relates to the field of surgical implants, and in particular to a method of treating biomedical material, and more particularly bioprosthetic heart valves and tracheas, to mitigate calcification when implanted in a mammalian body.

Importantly, the present invention is not limited to complete inhibition of calcification. It is enough that calcification is reduced.

As is well known, glutaraldehyde effects cross-linking of the proteins, e.g., collagen, within the tissue. Such cross-linking tends to make the tissue more durable and effects preservation thereof. It is known that cross-linked protein exhibits increased resistance to proteolytic cleavage and further that one of the major processes by which circulating blood may destroy tissue is via enzymatic activity which involves unfolding of the protein substrate in order to facilitate enzymatic hydrolysis. Cross-linking of the protein of a tissue makes the tissue resistant to such unfolding, and consequently tends to prevent deterioration thereof due to the enzymatic activity of blood.

The tissue then, as those skilled in the art well know, is trimmed and any non-biological components are then added thereto. For example, it is common to sew a heart valve to a valve holder which aids in the handling thereof and which may additionally function as a mount for the valve when implanted into a mammalian body (*Tissue Heart Valves*, ed. By M. I. Ionescu, publisher Butterworth Inc., Boston, Mass., U.S.A., 1979, particularly at pp. 146-172).

Calcitonin (also known as thyrocalcitonin) is a 32-amino acid linear polypeptide hormone with a molecular weight of 3454.93 daltons (Potts J T., Jr "Chemistry of the calcitonin": Bone Miner 1992; 16: 169-173), that is produced in humans primarily by the parafollicular cells (also known as C-cells) of the thyroid, and in many other animals in the ultimopharyngeal body (Pearse A G. The cytochemistry of the thyroid C cells and their relationship to calcitonin. Proc R Soc London B Bio Sci 1966; 164: 478-487). It acts to reduce blood calcium ($Ca^{2+}$), opposing the effects of parathyroid hormone (E A Agathos "The role of Calcitonin and Parathormone during the transient hypocalcemia following total thyroidectomy". PhD Thesis, University of Athens Medical School, 1988, Doi 10.12681/eadd/9351).

DETAILED DESCRIPTION OF THE PREFERRED EMBODIMENTS

The detailed description set forth below is intended as a description of the presently preferred embodiments of the invention, and is not intended to represent the only form in which the present invention may be constructed or utilized. The description sets forth the functions and sequence of steps for certain treatment embodiments of the invention.

In one embodiment, the method comprises placing the biological tissue for fixation and preservation in a buffered fixative solution (e.g. 0.5% at pH 7.4) and adding calcitonin. Thus, this embodiment involves the use of calcitonin at the time the fixative is used, i.e. together in a mixture. It is not intended that the present invention be limited to any particular source of calcitonin. However, salmon synthetic calcitonin (CT) is a convenient source.

As a pre-treatment step, the biomaterial can be first treated with a saline solution. For example, after harvesting, the biological tissue is rinsed and maintained in cold saline solution 0.9% NaCl (temperature between 2°-12° C.), typically for a period of 1-24 hours. Alternatively Hepa Saline Solution may be used. The Hepa saline solution can be made by the following formula: 20 liters of distilled water (Millipore-Direct-Q™ (18.2 MΩ·cm) with 180.01 g NaCl, 19.73 g NaHPO4, 121.72 g Na2HPO4, 20 ml HCL 1M (Ph 7.4).

In one embodiment, the method comprises placing the biological tissue for fixation and preservation in a buffered glutaraldehyde (Glut) solution 0.5% at pH 7.4, adding salmon synthetic calcitonin (CT), human calcitonin or of other origin, at various concentrations preferably between 0.1% up to 10%. In one embodiment, the first fixation process lasts for a first period (e.g. one to eight hours) and subsequently the biological tissues are embedded in or exposed to an accordingly fresh solution (of fixative and calcitonin) for a longer period (e.g. up to an including one week).

The reaction process can take place in a quiet environment. Alternatively, the reaction process can take place with stirring the solution between 50 rpm and 100 rpm at a temperature between 17° C. up to 37° C.

Following this novel anticalcification treatment of the present invention, the biological tissues can be sterilized (e.g. with a formaldehyde solution), as described in prior art, and then the tissues can be stored at buffered glutaraldehyde solution 0.25%-0.5% for a long period of time at room temperature, ready to use for mammal implantation. In another embodiment of the present invention, sterilization treatment can be achieved before the embedment of the biological tissue into this novel anticalcification treatment.

In another embodiment, calcitonin is used after the fixative treatment. As a pre-treatment step, the biomaterial can be first treated with a saline solution. For example, after harvesting, the biological tissue is rinsed and maintained in cold saline solution 0.9% NaCl (temperature between 2°-12° C.), typically for a period of 1-24 hours. Alternatively, Hepa Saline Solution may be used. The Hepa saline solution can be made by the following formula: 20 liters of distilled water (Millipore-Direct-Q™ (18.2 MΩ·cm) with 180.01 g NaCl, 19.73 g NaHPO4, 121.72 g Na2HPO4, 20 ml HCL 1M (Ph 7.4).

In this particular embodiment, the tissue is next fixed using a fixative (e.g. 0.5% buffered glutaraldehyde) solution at room temperature for at least 1 hour. Then the buffered fixative (e.g. glutaraldehyde) solution is changed and the tissues are left for fixation for a longer period (e.g. 1 to 7 days). In this particular embodiment, the method further comprises placing the biological tissue, after being fixed with glutaraldehyde or other fixative compounds, in contact with Calcitonin solution for a time between 4 hours up to 36 hours at a temperature between 17° up to 34° C.

EXPERIMENTAL

In one embodiment, the method comprises placing the biological tissue for fixation and preservation in a buffered glutaraldehyde (Glut) solution 0.5% at pH 7.4, adding salmon synthetic calcitonin (CT), such as Miacalcic® of Novartis Hellas A.B.E. In this experiment, two different concentrations of calcitonin were tested. One with 1 unit/100 ml (1%) and the other with 10 units/100 ml (10%). The first fixation process lasted one hour, at a pressure between 2-3 mmHg and subsequently the biological tissues were embedded in an accordingly new solution for one week.

Porcine aortic leaflets were selected as fresh tissue from a local slaughter house and were cut radially in three parts. Following harvesting, the biological tissue is rinsed and maintained in cold Hepa saline solution (temperature between 4°-12° C.) between two to six hours.

Three groups of tissue were created. Group I (Glut only), Group II (Glut with 1% CT) and Group III (Glut with 10% CT). All tissues were then implanted subdermally in three sets of 8 (Group I), 9 (Group II) and 9 (Group III) male Wistar rats of 12 days old (Center for Experimental Surgery, Biomedical Research Foundation of the Academy of Athens). The rats were selected along with their mother and had a free alimentation regime. All tissues were rinsed three times in normal saline solution for 10 minutes each time before implantation. Each rat received four fragments of tissue at the dorsum, through four separate incisions (two at each side) each of 1 cm long, with a technique we have previously described elsewhere (Agathos E A et al: "In vivo calcification of glutaraldehyde fixed cardiac valve and pericardium of Phoca Groenlandica": ASAIO 57(4):328-332, July/August 2011).

21 days later the rats were euthanized by inhalation of $CO_2$. All procedures were approved by the Animal Care Committee of the Academy of Athens and performed according to the Guide for the Care and Use of Laboratory Animals prepared by the Institutes of Laboratory Animal Resources, National Research Council and published by the National Academy Press, revised 1996 (NIH publication No. 85-23). The tissues were retrieved and after rinsing with distilled water 3 times, were lyophilized at −40° C. at high vacuum pressure of approximately 100 mmHg for 16 hours. The calcium content was then measured with flat atomic absorption technique.

For statistical analysis, the commercially available software package ANOVA Origin 8.0 for Windows (OriginLab Corporation, Northampton, Mass., USA) was used. P values of 0.05 or less were defined as a statistically significant difference.

RESULTS

The pre-implantation values for mg Ca/mg tissue of the various groups are listed in Table 1. Group I (control group) represents glutaraldehyde fixed tissues without anticalcification treatment, while Group II represents samples treated with buffered 1% CT solution and Group III represents samples treated with 10% CT solution.

The post implantation weight of the samples along with the values for mg Ca/mg tissue of the various groups are listed in Table 2, while Table 3 shows the cumulative results of Ca concentration in the various group and the statistical differences.

There was not significance difference between Groups II and III, even if Group II showed a less Ca concentration accumulation (×5.16) than Group III (×9.43) in the explanted tissues. All numeric data were expressed as mean±standard deviation (STDEV).

TABLE 1

Pre implantation Ca Content

|  | weight (gr) | mg Ca/gr tissue |
|---|---|---|
| Group I |  |  |
| Mean | 0.0039 | 1.79 |
| STDEV(±) | 0.0007 | 0.14 |
| Group II |  |  |
| Mean | 0.0110 | 4.78 |
| STDEV(±) | 0.0007 | 0.079 |
| Group III |  |  |
| Mean | 0.0120 | 2.88 |
| STDEV(±) | 0.0006 | 0.17 |

\* no statistical difference between the various groups
STDEV: Standard Deviation

TABLE 2

Post implantation Ca Content

|  | weight (gr) | mg Ca/gr tissue |
|---|---|---|
| Group I |  |  |
| Mean | 0.0086 | 126.95 |
| STDEV(±) | 0.0009 | 12.97 |
| Group II |  |  |
| Mean | 0.0458 | 24.69 |
| STDEV(±) | 0.0212 | 2.71 |
| Group III |  |  |
| Mean | 0.0453 | 27.16 |
| STDEV(±) | 0.0071 | 2.95 |

STDEV: Standard Deviation

TABLE 3

Cumulative results of post-implantation Ca concentration in the Various group and statistical difference

| Group I (Glut only) 8 rats | Group II (1% CT) 8 rats | Group III (10% CT) 9 rats |
|---|---|---|
| 126.95 ± 12.97 | 24.69 ± 2.71 $p < 0.05$* | 27.16 ± 2.95 $p < 0.05$** |
|  | $p = ns$*** |  |

*The statistical difference between Group II and Group I
**The statistical difference between Group III and Group I
***The statistical difference between Group II and Group III It is understood that the analytical method for treating glutaraldehyde fixed biological tissue described herein represents only a presently preferred embodiment of the present invention. Various modifications and additions may be made to such embodiment without departing from the scope of the invention. For example, various fixing agents, such as aldehydes other than glutaraldehyde or other chemicals, may exhibit properties, similar to those of glutaraldehyde so as to make them suitable for use in the present invention and, thus, may likewise be utilized. Accordingly, these and other modifications and additions may be obvious to those skilled in the art and may be implemented to adapt the present invention for use in a variety of different applications.

The invention claimed is:

1. A method for treating biological tissue, comprising exposing said tissue to a mixture of a fixative and Calcitonin in solution so as to create treated biological tissue, wherein said biological tissue is selected from the group consisting of porcine aortic valves and pericardium, bovine pericardium, equine pericardium, seal aortic, pulmonary valve and pericardium, kangaroo aortic valve and pericardium and human, seal, porcine and dog trachea.

2. The method of claim 1, wherein the fixative is glutaraldehyde.

3. The method of claim 1, wherein said Calcitonin is human Calcitonin.

4. The method of claim 1, wherein said Calcitonin is synthetic Calcitonin.

5. The method of claim 1, wherein said Calcitonin is salmon Calcitonin.

6. The method of claim 1, wherein said exposing is for a time period between 4 and 36 hours.

7. The method of claim 1, wherein said exposing is done at a temperature between 17° and 37° C.

8. The method of claim 1, wherein the solution is stirred during said exposing.

9. The method of claim 8, wherein said stirring is between 50 rpm and 100 rpm.

10. The method of claim 1, further comprising implanting said treated biological tissue in a human or animal so as to create an implanted biological tissue.

11. The method of claim 10, wherein said implanted biological material comprises one or more arterial conduits of human or animal origin.

12. A method for treating biological tissue, comprising a) exposing said tissue to a mixture of a fixative and Calcitonin in solution so as to create treated biological tissue; and b) implanting said treated biological tissue in a human or animal so as to create implanted biological tissue, wherein said implanted biological tissue is selected from the group consisting of porcine aortic valves and pericardium, bovine pericardium, equine pericardium, seal aortic, pulmonary valve and pericardium, kangaroo aortic valve and pericardium and human, seal, porcine and dog trachea.

13. The method of claim 12, wherein the fixative is glutaraldehyde.

14. The method of claim 12, wherein said Calcitonin is human Calcitonin.

15. The method of claim 12, wherein said Calcitonin is synthetic Calcitonin.

16. The method of claim 12, wherein said Calcitonin is salmon Calcitonin.

17. The method of claim 12, wherein said exposing is for a time period between 4 and 36 hours.

18. The method of claim 12, wherein said exposing is done at a temperature between 17° and 37° C.

19. The method of claim 12, wherein the solution is stirred during said exposing.

20. The method of claim 19, wherein said stirring is between 50 rpm and 100 rpm.

21. The method of claim 12, further comprising rinsing said treated biological tissue after step a) and before step b).

22. The method of claim 12, wherein said implanted biological material comprises one or more arterial conduits of human or animal origin.

23. The method of claim 12, wherein said implanted biological material comprises one or more venous conduits of human or animal origin.

\* \* \* \* \*